US00PP21882P3

(12) United States Plant Patent
Dutschke

(10) Patent No.: US PP21,882 P3
(45) Date of Patent: Apr. 26, 2011

(54) ***EUCALYPTUS CLADOCALYX* PLANT NAMED 'EUC78'**

(50) Latin Name: *Eucalyptus cladocalyx*
Varietal Denomination: EUC78

(76) Inventor: Nathan Dutschke, Richmond (AU)

( * ) Notice: Subject to any disclaimer, the term of this patent is extended or adjusted under 35 U.S.C. 154(b) by 0 days.

(21) Appl. No.: 12/383,329

(22) Filed: Mar. 23, 2009

(65) Prior Publication Data

US 2009/0249523 P1 Oct. 1, 2009

(51) Int. Cl.
*A01H 5/00* (2006.01)

(52) U.S. Cl. ..... Plt./216

(58) Field of Classification Search ..... Plt./216
See application file for complete search history.

*Primary Examiner* — Susan B McCormick Ewoldt

(57) ABSTRACT

'EUC78' is a distinctive variety of *Eucalyptus cladocalyx,* which is characterized by its combination of red purple foliar coloration including immature and intermediate leaves, stems and bark. 'EUC78' has use as an ornamental tree in landscape and amenity horticulture and as cut foliage for the floral industries.

2 Drawing Sheets

Latin name of the genus and species: The Latin name of the novel variety disclosed herein is *Eucalyptus cladocalyx* 'EUC78'.

Variety denomination: The inventive variety of *Eucalyptus cladocalyx* disclosed herein has been given the variety denomination 'EUC78'.

BACKGROUND OF THE INVENTION

The present invention relates to a new and distinct variety of evergreen perennial *Eucalyptus cladocalyx,* which has been named 'EUC78'. *Eucalyptus cladocalyx* is an Australian native tree that grows to a mature height usually from 10 to 20 meters tall and 5 to 10 meters wide and is used as an ornamental tree in landscape and amenity horticulture. The common name of this species is 'Sugar Gum'. The novel variety described herein details a red purple foliar form which is distinct from the common green foliar form. It has distinctive leaf and stem coloration including immature leaves and stems and bark as well as mature leaves, stems and bark.

An application for plant breeders' rights for 'EUC78' has been lodged with the Australian Plant Breeders Rights Office, and was received on 26 Mar. 2008 (under application No. 2008/084). An application for an Australian patent has been lodged with IP Australia and was filed on 16 Feb. 2009 under application number 2009900631.

Parentage: The cultivar 'EUC78' was discovered in 2005 in St Agnes, Adelaide, South Australia. The parent form is characterized by its dull green foliage color. Seed from open pollinated *Eucalyptus cladocalyx* (unpatented, common form) were sown and 2000 seedlings were germinated and grown on. The resultant seedlings were monitored on a regular basis and one of the seedlings was observed to exhibit a red purple foliage color which was different to the dull green foliage color of the other seedlings. The selection criterion for 'EUC78' was this novel red purple foliar coloration. This seedling was isolated and potted into a 50 mm tube for further growth and observation of its characters. It was found that the red colored immature leaves matured to a darker purple intermediate leaf color. The color of the stem was also found to be a dark purple color which remained as a stable trait as the plant grew to a larger size.

These foliar characters were observed to remain stable as the plant matured. Plants produced sexually by seed propagation are known to show variation in morphological characters. A stable method of reproducing the invention was developed by using an asexual method of propagation known as grafting, whereby shoots of the inventive plant are grafted to *E. cladocalyx* rootstocks. Cutting propagation of the variety may also be used to reproduce the invention.

The inventive variety was recognised to have merit for use as an ornamental tree in landscape and amenity horticulture with the plant being grown in a range of container sizes including 200 mm pots which are suited to supply the retail nursery market and larger container sizes, typically 300 mm to 800 mm, or bag sizes from 25 L to 400 L for the commercial landscape market.

The potential of the inventive variety as a cut foliage for the floral industry was recognised and branches can be used for this purpose. Vase life trials were conducted to establish this suitability and it was found a vase life of 5 to 12 days may be expected, depending on treatment and environmental conditions. The novel coloration of the inventive variety was considered to be a means of negating the need for traditional dye treatments as used in the floral industries.

Asexual reproduction. The new variety 'EUC78' was first asexually propagated by grafting in the state of New South Wales, Australia in 2006. The distinctive characteristics of cultivar 'EUC78' have remained stable and true to type through successive cycles of asexual propagation. Cutting propagation of the variety may also be used to reproduce the invention.

SUMMARY OF THE INVENTION

'EUC78' is a distinctive variety of *Eucalyptus cladocalyx,* which is characterized by its combination of red purple foliar coloration including immature and intermediate leaves, stems and bark. 'EUC78' has use as an ornamental tree in landscape and amenity horticulture and as cut foliage for the floral industries.

DETAILED BOTANICAL DESCRIPTION OF THE VARIETY

Figure 1:
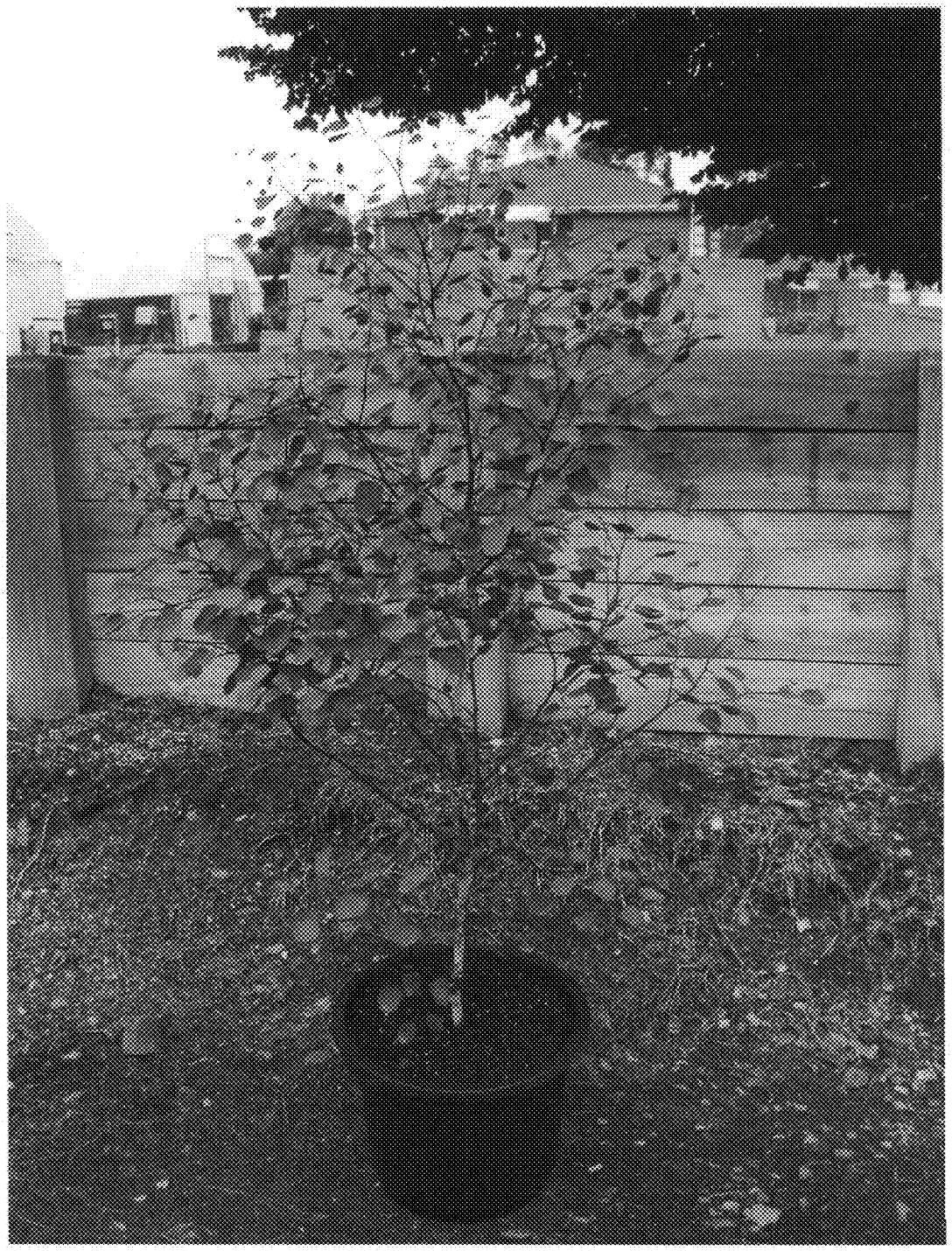
FIG. 1 shows a *Eucalyptus cladocalyx* 'EUC78' plant at approximately 12-months of age. The plant was propagated in a greenhouse and was transferred to the field at six months and grown out in full sun.

The following is a detailed botanical description of a new and distinct variety of *Eucalyptus cladocalyx* known as 'EUC78' based upon observations of 12-month old plants grown in 400 mm nursery pots in full sun in open beds in Clarendon, New South Wales, Australia during 2008-2009. Plant observations and descriptions were taken in late summer 2009.

Those skilled in the art will appreciate that certain characteristics will vary with older or, conversely, with younger plants. 'EUC78' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2007 edition.

'EUC78' is an evergreen perennial *Eucalyptus cladocalyx.* 'EUC78' is an upright to spreading tree with a single trunk when left unpruned or a strongly branched and dense growth habit when pruned. 'EUC78' has red purple foliar coloration including immature and intermediate leaves, stems and bark. 'EUC78' has red purple stems which when immature are almost black in appearance. As the seasons growth matures the deep colored bark on the branches and trunk peels away during the summer months revealing a contrasting smooth greyish bark.

These characteristics are unusual for *Eucalyptus cladocalyx,* as these plants usually have a dull green leaf color and grey green stems. A botanical description of 'EUC78' and comparisons with the parent form of *Eucalyptus cladocalyx* are provided below.

Technical Description of the Variety

Plant characteristics: Growth habit upright to spreading, bushy when pruned, height medium to tall, a one year old grafted plant in a 400 mm pot being approximately 1.5 m tall (not yet recorded for a fully mature tree). Branching is acute with an observed, average branch diameter of 1.4 cm. At one year of age the grafted plant was observed to have a trunk diameter (diameter at breast height) of 2.6 cm.

Stems: New stem has a smooth surface texture, color is darker on light facing surfaces (RHS 200A) and lighter and more purple reddish on surfaces with indirect light exposure (approximately RHS 187A).

Leaves: The simple leaves are arranged decussately in the immature, intermediate and mature plant. Leaf texture in all stages is smooth and free of pubescence. Immature leaves, upper and lower side color greyed orange approximately RHS 166B. Intermediate leaves: Attitude horizontal to semi-erect, length medium (range 4.5 to 5.5 cm), width medium (range 4.5 to 5.5 cm), upper side color dull grey green to purple corresponding nearest to RHS 202A with pinnate venation 200A to 187A, lower side color corresponding nearest to 202B to N189C, variegation absent, shape reniform, apex broad, rounded, occasionally retuse, cross section flat to slightly concave, margin entire, margin color 200A, upper side midrib color 200A, lower side midrib color 200A, petiole length medium (range 2.2-2.8 cm) and petiole diameter medium (range 2-3 mm). The petiole color also corresponds to RHS 200A.

Flowers and fruiting: Flowering characteristics of 'EUC78' have yet to be recorded.

Cold and heat tolerance: 'EUC78' has not yet been observed under all conditions. 'EUC78' is heat tolerant. It adapted well to the high heat conditions greater than 40 degrees Celsius during summer in Clarendon, New South Wales, Australia without any noticeable damage. It has survived light to moderate frosts. Testing for environmental tolerances is ongoing.

Drought tolerance: Good drought tolerance typical of the species once established. 'EUC78' has not yet been observed under all conditions. Testing for environmental tolerances is ongoing.

Pest resistance: No known pests.

Cultural conditions: 'EUC78' can tolerate low nutrient conditions; it does not like continually wet soil conditions, but can tolerate well-draining sandy soils to very heavy clay soils.

Comparisons with other *Eucalyptus cladocalyx*

'EUC78' has red purple foliar coloration including immature and intermediate leaves, stems and bark. 'EUC78' has red purple stems which when immature are almost black in appearance. As the seasons growth matures the deep colored bark on the branches and trunk peels away during the summer months revealing a contrasting smooth greyish bark.

These characteristics are unusual for *Eucalyptus cladocalyx,* as these plants usually have a dull green leaf color and immature stem color of yellow green maturing to orange brown stems. There have been no other varieties of this species selected to date and the nursery and landscape trades have traditionally grown the common species form of *Eucalyptus cladocalyx.*

Figure 2:
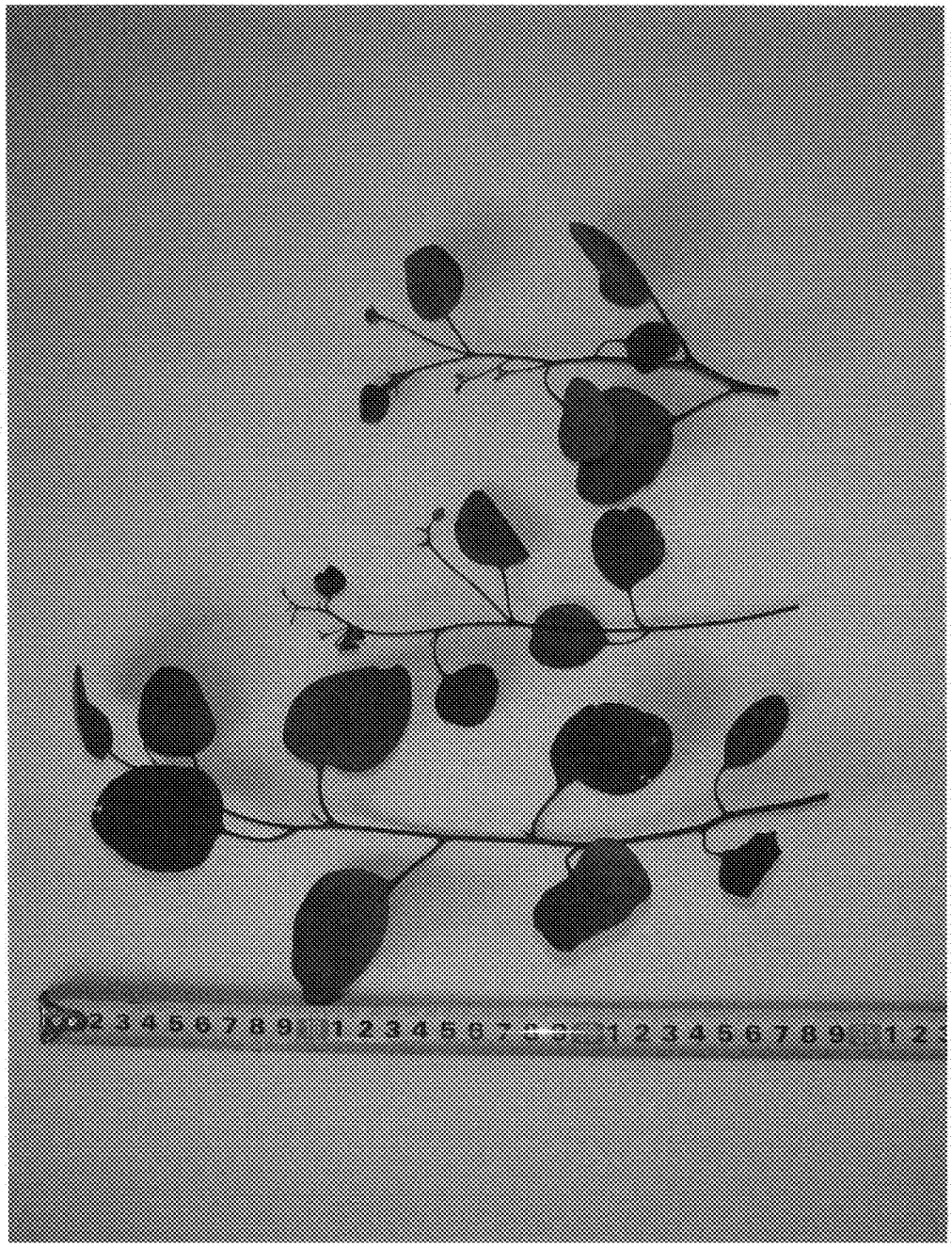
FIG. 2 shows the color of new growth including stems and upper and lower side of leaves of 'EUC78'.

The appearance of 'EUC78' foliage is an overall dark red purple to black coloration. FIG. 1 and FIG. 2 illustrate the unusual coloration of the foliage.

A trial of 'EUC78' is being carried out at Clarendon, NSW. The initial data are presented in Table 1 below.

TABLE 1

| | *Eucalyptus cladocalyx* Variety | |
|---|---|---|
| Characteristic | 'EUC78' | *Eucalyptus cladocalyx* |
| Stem: color of bark | red purple to black | orange brown |
| Immature stem: color of bark | red purple to black | yellow green |
| Intermediate leaf: color | grey green to purple | green |
| Leaf: margin color | red purple | green |

That which is claimed is:

1. A new and distinct variety of *Eucalyptus cladocalyx* plant named 'EUC78', substantially as described and illustrated herein.

* * * * *